(12) United States Patent
Peyman

(10) Patent No.: US 6,395,294 B1
(45) Date of Patent: *May 28, 2002

(54) METHOD OF VISUALIZATION OF THE VITREOUS DURING VITRECTOMY

(76) Inventor: Gholam A. Peyman, 8654 Pontchartrain Blvd. Apt. 1, New Orleans, LA (US) 70124

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/482,779

(22) Filed: Jan. 13, 2000

(51) Int. Cl.$^7$ .................................................. A61F 2/00
(52) U.S. Cl. ...................... 424/427; 424/422; 424/423; 424/450; 424/489; 604/19; 623/4.1
(58) Field of Search ........................... 623/4.1; 424/427, 424/450, 422, 423, 489; 604/19

(56) References Cited

U.S. PATENT DOCUMENTS 5,597,381 A * 1/1997 Rizzo, III ....................... 623/4

OTHER PUBLICATIONS

Gaudric et al., *An aspirating forceps to remove the posterior hyaloid in the surgery of full–thickness macular holes*, Retina 16:261–263 (1996).

Shinoda et al., *A new technique for separaton of posterior vitreous in vitreous surgery*, Ophthalmic Surg Lasers 30:588–590 (1999).

Ruiz–Moreno et al., *Dissection of the posterior hyaloid*, Arch Opthalmol 116:1392–1393 (1998).

Challa et al., *Exudative macular degeneration and intravitreal triamcinolone: 18 month follow up*, Aust NZ J Ophthalmol, 26:277–281 (1998).

Johnson et al., *Idiopathic macular holes: observations, stages of formation and implications for surgical intervention.*, Ophthalmology 95:917–924 (1988).

Graham et al., *Intravitreal Injection of Dexamethasone*, Arch Opthalmol vol. 92, Aug. 1974, pp. 149–154.

Peyton et al., *Intravitreal Surgery: Principles and Practice*, Appleton and Lange, Norwalk, CT, Ch. 22 pp. 958–971, Ch. 24 pp. 983–989, Ch. 20 pp. 867–868, and ch. 21 pp. 934–936, (1994).

Mein et al., *Recognition and removal of the posterior cortical vitreous during vitreoretinal surgery for impending macular hole*, Am J Opthalmol 111:611–613 (1991).

Danis et al., *Short–term visual outcome of exudative age–related macular degeneration treatment with intravitreal triamcinolone acetonide*, Invest Ophthalmol Vis Sci, 40 No. 4 (Suppl):S316 B583, 1675–B583, (1999).

Han et al., *Surgical excision of the attached posterior hyaloid*, Arch Opthalmol 106:998–1000 (1988).

McCuen et al., *The lack of toxicity of intravitreally administered triamcinolone acetonide*, Am J Opthalmol 91:785–788 (1981).

(List continued on next page.)

Primary Examiner—Thurman K. Page
Assistant Examiner—L. Di Nola Baron
(74) Attorney, Agent, or Firm—Wood, Herron & Evans, LLP

(57) ABSTRACT

A composition for rendering a vitreous cavity visible during a surgical procedure to alleviate a structural disorder caused by the vitreous in an eye, and a method of using the composition. The composition is a vitreous delineating agent that is translucent, opaque or semi-opaque and is in a formulation that may be a solution, a suspension or an emulsion. The agent may be a liposome or microsphere that may additionally contain a therapeutic agent. In use, the agent marks or delineates the vitreous cavity, allowing a surgeon to clearly visualize the entire cavity. Use of the method improves accuracy of a vitrectomy and thus prevents suboptimal outcomes or the need for repeated procedures.

15 Claims, 1 Drawing Sheet

(1 of 1 Drawing Sheet(s) Filed in Color)

OTHER PUBLICATIONS

Nabih et al., *Toxicity of high–dose intravitreal dexamethasone*, International Opthalmology, 15: 233–235, 1991.

Tano et al., *Treatment of intraocular proliferation with intravitreal injection of triamcinolone acetonide*, Am J Ophthalmol, 90:810–816 (1980).

Wilson et al., *Treatment with intravitreal steroid reduces blood–retinal barrier breakdown due to retinal photocoagulation*, Arch Ophthalmol, 110:1155–1159 (1992).

Ryan et al., *Use of intravitreal autologous blood to identify posterior cortical vitreous in macular hole surgery*, Arch Ophthalmol, 113:822–238 (1995).

* cited by examiner

METHOD OF VISUALIZATION OF THE VITREOUS DURING VITRECTOMY

This application is supported in part by the United States Public Health Service, Grant No. EY02377, from the National Eye Institute, National Institutes of Health.

FIELD OF THE INVENTION

The invention is directed generally to a surgical method, and more specifically to a composition for use during ophthalmic surgery.

BACKGROUND

In the eye, the cavity between the lens and the retina is filled with a clear, jelly-like semisolid substance termed the vitreous body or vitreous. Its volume is fixed and is relatively permanent. The vitreous is surround by the hyaloid membrane. In pathological conditions such as macular hole, vitreomacular traction syndrome and proliferative vitreoretinopathy, the posterior cortical vitreous (posterior hyaloid) is partially or completely attached to the retina and the inner limiting membrane and thus may provide a source of traction. The attachment may also serve as a scaffold for fibrous proliferation in proliferative diabetic retinopathy.

Proliferative vitreoretinopathy, a major cause of failure of retinal reattachment surgeries, involves cellular proliferation on the anterior and posterior surfaces of the retina. Cellular vitreous strands and membranes form and contract, creating a new retinal detachment and usually loss of some vision. Both clinical and experimental evidence suggests that breakdown of the blood-retinal barrier is important in the pathogenesis of proliferative vitreoretinopathy, stimulating basic cellular processes of growth, chemotaxis, migration, and proliferation. This loss of blood retinal barrier integrity results in an increase in the protein content of intraocular fluid, which may stimulate intraocular fibrin formation and creation of a scaffold of preretinal cellular membranes. These membranes subsequently contract to create a tractional retinal detachment typical of proliferative vitreoretinopathy.

A patient suffering from any of these conditions may undergo a surgical procedure, such as pars plana vitrectomy, in an attempt to alleviate these conditions. However, the surgical procedure itself also produces complications. Postoperative intraocular fibrin formation is a common complication of vitrectomy surgery and penetrating ocular injury. Extensive intraocular surgery, epiretinal membrane dissection in proliferative vitreoretinopathy, and inflammatory conditions such as endophthalmitis and uveitis exaggerate postoperative intraocular fibrin formation because of increased vascular permeability. Additional surgical procedures such as endophotocoagulation, cryopexy, scleral buckling, and intraocular gas introduction also exacerbate the intraocular inflammation. Various other factors have been implicated in fibrin formation including a preoperative retinal detachment, combined surgery (lensectomy and vitrectomy), and severe or prolonged hypotony. Eyes with proliferative diabetic retinopathy are especially susceptible to fibrin formation because long-term disease damages the blood retinal barrier. Laser and cryopexy have been shown experimentally to compromise the blood retinal barrier, enhancing the ability of the vitreous to stimulate retinal pigment epithelium migration and proliferation, thereby increasing the incidence of tractional retinal detachment. Additionally, a high percentage of surgeries fail in severely diseased, previously operated, and uveitic eyes, and effective treatment of retinal detachment with a proliferative vitreoretinopathy component, severe proliferative diabetic retinopathy with traction retinal detachment, and persistent ocular inflammatory disease remain a challenge for vitreoretinal specialists.

During surgery the transparency of vitreous makes it difficult for the surgeon to visualize and hence completely remove the vitreous and posterior hyaloid. A surgeon performing a procedure may not be absolutely certain whether posterior hyaloid separation and complete vitrectomy has occurred. Many surgical techniques have been described which attempt to aid in removal of the posterior hyaloid during pars plana vitrectomy. These include the use of various cannulas and forceps with active or passive suction applied to engage and separate the posterior hyaloid from the retina. New drug delivery devices have improved surgical outcomes and controlled intraocular inflammation. Also, Ryan et al. have described the use of autologous blood for improved visualization of cortical vitreous during posterior hyaloid separation. None of these are completely satisfactory, however, and use of blood has several drawbacks: blood disperses into the vitreous cavity and is likely to obscure visualization during vitrectomy, and has the potential of causing postoperative inflammation and proliferative vitreoretinopathy.

A need still exists for surgical correction of the defect, but with improved accuracy and precision so that complications, as well as reduced discomfort, inconvenience and expense to the patient, may be minimized. Thus, methods and agents to improve the visualization of the vitreous during a surgical procedure, and hence to ensure accuracy of the procedure, are desirable to achieve better functional and anatomical outcomes.

SUMMARY OF THE INVENTION

The invention is directed to a method to alleviate a structural disorder of an eye. A vitreous delineating agent is injected into the eye in an effective amount to allow the vitreous to be visible to a surgeon, enabling the surgeon to alleviate the disorder. The agent may be a therapeutic agent, an inert agent, or an inert agent that contains a therapeutic agent, such as a microsphere or liposome containing a therapeutic agent. In one embodiment the agent is a corticosteroid but may be, for example, an antiinfective agent, an immunosuppressant agent, an antiproliferative agent, and/or an antiangiogenesis agent. The agent may be in a formulation such as a solution, an emulsion, or a suspension.

The invention is also directed to a method to alleviate a structural disorder of an eye by injecting a corticosteroid formulation into the eye in an effective amount to enable a surgeon to visualize the vitreous and to thus alleviate the disorder. The corticosteroid formulation may also contain an additional therapeutic agent, and/or may be incorporated into a vesicle such as a microsphere or a liposome.

The invention is additionally directed to a composition for visualizing a vitreous cavity in a mammalian eye during surgery. The composition is an injectable formulation of a vitreous delineating agent that associates with vitreous fibers in the eye to render the vitreous cavity visible to the surgeon. The formulation of the agent may be translucent, opaque, or semi-opaque.

These and other aspects of the invention will be apparent in light of the following figures and detailed description.

BRIEF DESCRIPTION OF THE FIGURES

The file of this patent contains at least one drawing executed in color. Copies of this patent with color drawings

DETAILED DESCRIPTION

Figure 1:
FIG. 1 is a photomicrograph of an eye injected with one agent of the invention prior to surgery.

The use of one or more vitreous delineating agents to improve visualization of the vitreous during surgery to alleviate a structural disorder of an eye is disclosed. Delineation of the vitreous assists the surgeon in separation of the posterior hyaloid and complete removal of vitreous during the procedure, such as a pars plana vitrectomy. The agent is mixed into the vitreous, increasing the visualization of its strands and the posterior hyaloid. The visible vitreous delineating agent, either as a solution, suspension or emulsion, "hangs onto" the vitreous fibers and, in doing so, marks the entire vitreous cavity. The delineating agent may also serve as a therapeutic agent, inert agent, or a combination thereof. The agent becomes visibly trapped in the gel structure of the vitreous; it delineates or demarcates the vitreous and in effect "lights up" the vitreous structure. This improves visualization of the vitreous and its posterior hyaloid for the surgeon.

The agent must be visible to the surgeon during surgery; that is, the agent must itself be translucent (transmitting light but causing sufficient diffusion to eliminate perception of distinct images), opaque (impenetrable by light), or semi-opaque (partially impenetrable by light), or be rendered translucent, opaque or semi-opaque. Visualization may be with the naked eye or with the assistance of instrumentation such as an operating microscope. The agent may be a therapeutic agent such as an anti-inflammatory agent, anti-microbial agent, anti-angiogenesis agent, or antiproliferative agent, or an inert substance such as a blank microsphere or liposome, or combinations of the above (for example, a microsphere or liposome containing any of the above therapeutic agents), as long as they are visible during the surgical procedure. A combination of agents may be used.

In one embodiment the agent is a corticosteroid. Corticosteroids are commonly used after ophthalmic procedures to reduce the morbidity of ocular inflammatory diseases, since they have a high level of antimitotic activity and an inhibitory effect on fibroblast growth. Corticosteroids block the enzyme phospholipase A2 and prevent the production of both prostaglandins and leukotrienes, which are mediators responsible for the breakdown of the blood retinal barrier. For example, the corticosteroid dexamethasone has a significant effect on the blood retinal barrier breakdown, and intravenous solumedrol quiets diabetic eyes with rubeosis iridis. Tano et al. (*Am J Ophthalmol* 89 (1980) 131–136) found a single injection of 1 mg of dexamethasone in the vitreous inhibited fibroblast growth. In another study, a dose of 2 mg of dexamethasone sodium phosphate did not show retinal toxicity (Nabih et al., *Int Ophthalmol* 15 (1991) 233–235). Low dose (4 µg/mL) steroids added to the vitrectomy infusion fluid have been shown to be useful in reducing postoperative inflammation (Graham and Peyman, *Arch Ophthalmol* 92 (1974)149–154). Each of the above references are expressly incorporated by reference herein in its entirety.

Corticosteroid administration can be topical, subconjunctival (peribulbar/sub-Tenon's injection), or systemic. Because prolonged systemic corticosteroid use has undesired side effects, local administration is preferred whenever possible. The intravitreal concentration of dexamethasone may be higher when administered periocularly than orally. Steroid levels in the anterior segment may be higher following peribulbar injection compared with topical or subconjunctival administration. Also, peribulbar injection has fewer systemic side effects, but rarely can cause complications, such as retrobulbar hemorrhage, ocular perforation, increase in intraocular pressure, and a detectable drug level in the fellow eye. Additionally, peribulbar injection is difficult to perform in eyes which have had previous buckling procedures or those with high myopia. Intravitreal injections of hydrocortisone reportedly showed no difference in aqueous formation rate and outflow facility compared with eyes receiving an injection of saline, but both groups developed an increased intraocular pressure because of a decrease in outflow facility.

Any agent that is translucent, opaque or semi-opaque and hence visible during the surgical procedure may be used. The agent should be non-toxic at an administered level, and should be naturally cleared from the eye and not require surgical removal. Preferably, the agent has a particle size less than about 50 µm. The agent may provide an additional therapeutic benefit to the patient, or the agent may be inert.

Corticosteroids have been administered after pars plana vitrectomy to provide long term steroid therapy. For example, triamcinolone acetonide (commercially available as Kenalog®, Apothecon, Bristol-Squibb Co., Princeton, N.J.), is a synthetic corticosteroid with marked anti-inflammatory action, and slow delivery of the active ingredient over a longer period of time. Its use for the control of postoperative inflammation and control of proliferative vitreoretinopathy following vitrectomy is well documented. The aqueous suspension of triamcinolone in the vitreous provides a good visualization of the vitreous during vitrectomy, and behaves optically like the clinical condition "asteroid hyalosis". The suspension particles are trapped in the gel structure of the vitreous and clearly stand out, in contrast to a free-floating suspension of particles of infusion fluid where the vitreous has been removed. This clearly demarcates areas where the vitreous is present and demarcates its boundaries during vitrectomy. Any residual triamcinolone suspension may be removed with a vitreous cutter as the vitrectomy proceeds. Triamcinolone may be administered via different routes (topical, subconjunctival, periorbital, and intravitreal) and is reportedly effective in the treatment of a wide variety of noninfectious inflammatory conditions of the eye. It has no retinal toxicity in vitrectomized and nonvitrectomized eyes in a dosage of 2–4 mg, and is well tolerated in the rabbit, primate, and human eyes. Because of its hydrophobicity, triamcinolone provides therapeutic levels for at least three months after intravitreal injection. The crystalline nature of the drug, together with its sequestration in the vitreous, results in its slow dissipation, ensuring an effective concentration near the retina for an extended period.

Intravitreal triamcinolone has been shown experimentally to inhibit angiogenesis, to reduce the breakdown of the blood retinal barrier, to reduce the incidence of proliferative vitreoretinopathy and subsequent retinal detachment, and to inhibit preretinal and optic disc neovascularization. Because common causes of vitreoretinal morbidity, such as inflammation, fibrin and fibrous tissue development, and neovascularization are caused by conditions that may be limited by steroid administration, one proposed use of triamcinolone acetonide is as an adjunct in the treatment of vitreoretinal morbidity to provide a more efficient long-term local drug delivery, while avoiding the systemic side effects caused by other forms of corticosteroids.

While a corticosteroid such as triamcinolone acetonide has been demonstrated, the inventive method may be performed using any agent that is a translucent, semi-opaque, or opaque suspension, solution or emulsion, or that may be rendered translucent, semi-opaque or opaque. Other corticosteroids may be used, such as natural and synthetic corticosteroids which include, but are not limited to, cortisol, cortisone (11-dehydrocortisol), corticosterone, 11-desoxycorticosterone, 11-desoxycortisol, aldosterone, prednisolone ($\Delta^1$-Cortisol), 6α-methylprednisolone, triamcinolone (9α-fluoro-16α-hydroxyprednisolone), paramethasone (6α-fluoro-16α-methylprednisolone), betamethasone (9α-fluoro-16β-methylprednisolone), dexamethasone (9α-fluoro-16α-methylprednisolone), fludrocortisone (9α-fluorocortisol), fludrocortisone acetate, tetrahydrocortisol, prednisone ($\Delta^1$-cortisone), cortisol (hydrocortisone) (Cortef™, Hydrocortone™ and others), cortisol (hydrocortisone) acetate (Hydrocortone Acetate™, cortisol (hydrocortisone) sodium phosphate (Hydrocortone Phosphate™), cortisol (hydrocortisone sodium succinate) A-Hydrocort, Solu-Cortef™) betamethasone sodium phosphate (Celestone Phosphate™ and others), betamethasone sodium phosphate (Celestone Soluspan™ and others), cortisone acetate (Cortone Acetate™) dexamethasone acetate (Decadron-La™ and others), dexamethasone sodium phosphate (Decadron Phosphate™, Hexadros Phosphate™ and others), methylprednisolone acetate (Depo-Medrol™, Medrol Acetate™ and others), methylprednisolone sodium succinate (A-Methapred™, Solu-Medrol™), prednisolone acetate (Econopred™ and others), prednisolone sodium phosphate (Hydeltrasol™ and others), prednisolone tebutate (Hydeltra-T.B.A.™ and others), triamcinolone diacetate (Aristocort™, Kenacord Diacetate™ and others), triamcinolone hexacetonide (Aristopan™).

In other embodiments of the method, the agents may be incorporated into vesicles which provide a translucent, semi-opaque or opaque injectable. Examples of such vesicles include liposomes or microspheres, for example, poly (glycolic) or poly(lactic) acid microspheres. Incorporation of agents into liposomes or microspheres may be performed by routine procedures as known to one skilled in the art.

In still other embodiments of the invention, a mixture of the same agents, such as mixture of corticosteroids, or a mixture of different agents, such as a corticosteroid and another therapeutic agent, may be used. The therapeutic agent may be, for example, ocular anti-infective agents such as penicillins (ampicillin, aziocillin, carbenicillin, dicloxacillin, methicillin, nafcillin, oxacillin, penicillin G, piperacillin, and ticarcillin), cephalosporins (cefamandole, cefazolin, cefotaxime, cefsulodin, ceftazidime, ceftriaxone, cephalothin, and moxalactam), aminoglycosides (amikacin, gentamicin, netilmicin, tobramycin, and neomycin), miscellaneous agents such as aztreonam, bacitracin, ciprofloxacin, clindamycin, chloramphenicol, cotrimoxazole, fusidic acid, imipenem, metronidazole, teicoplanin, and vancomycin), antifungals (amphotericin B, clotrimazole, econazole, fluconazole, flucytosine, itraconazole, ketoconazole, miconazole, natamycin, oxiconazole, and terconazole), antivirals (acyclovir, ethyldeoxyuridine, foscarnet, ganciclovir, idoxuridine, trifluridine, vidarabine, and (S)-1-(3-dydroxy-2-phospho-nyluethoxypropyl) cytosine (HPMPC)), antineoplastic agents (cell cycle (phase) nonspecific agents such as alkylating agents (chlorambucil, cyclophosphamide, mechlorethamine, melphalan, and busulfan), anthracycline antibiotics (doxorubicin, daunomycin, and dactinomycin), cisplatin, and nitrosoureas), antimetabolites such as (antipyrimidines (cytarabine, fluorouracil and azacytidine), antifolates (methotrexate), antipurines (mercaptopurine and thioguanine), steroids, bleomycin, vinca alkaloids (vincrisine and vinblastine), podophylotoxins (etoposide (VP-16)), and nitrosoureas (carmustine, (BCNU))), immunosuppressant agents such as cyclosporin A and SK506, and anti-angiogenesis agents such as anti-inflammatory or suppressive factors (inhibitors) that prevent endothelial cell proliferation, and inhibitors of proteolytic enzymes such as plasminogen activator inhibitors. Doses for systemic, topical and sub-conjunctival administration of the above agents, as well as Intravitreal dose and vitreous half-life may be found in *intravitreal Surgery Principles and Practice*, Peyman G A and Shulman, J Eds., $2^{nd}$ edition, 1994, Appleton-Longe, the relevant sections of which are expressly incorporated by reference herein.

The invention will be further appreciated in light of the following example.

EXAMPLE

Three standard surgical incisions of the sclera (sclerotomy) are made; no prior core vitrectomy is performed. A vitreous delineating agent that is visible or is rendered visible, such as triamcinolone acetonide aqueous suspension (40 mg/ml), is injected into the midvitreous cavity just above the retina. One to two drops (about 0.33–0.67 ml) are injected through one of the sclerotomies employing the tip of a needle (30 gauge) which may be visualized in the midvitreous. This visible suspension is dispersed into the vitreous cavity with gentle movements of a light pipe and vitrector.

Active aspiration with a vitrectomy probe or soft cannulated extrusion needle is applied to a maximum of 200–300 mm Hg just nasal to the optic disc. As shown in FIG. 1, the agent delineates the boundary of the posterior hyaloid (arrow), which is being separated from the retina by the vitrectomy port. The posterior cortical vitreous is seen stretched and elevated from the surface of retina during this surgical maneuver; the subsequent creation of a posterior vitreous detachment combined with cutting allows infusion fluid to rush into the space created, rapidly expanding the posterior hyaloid space. The boundary between posterior cortical vitreous and the fluid-filled posterior hyaloid space is thus easily visualized because of the different characteristics of agent in the fluid filled posterior hyaloid space and the formed gel of the vitreous. Agent particles in the fluid filled space are freely mobile, as compared to agent particles trapped in the gel structure of the vitreous. The lateral limit of the posterior hyaloid separation is thus visibly demarcated by agent particles suspended in the vitreous gel. This allows the surgeon to accurately visualize the posterior hyaloid and vitreous during the procedure, and to completely and easily remove the posterior hyaloid and formed vitreous. Complete removal can be confirmed by visualizing the granules of the agent layering on the surface of the retina.

Figure 2:
FIG. 2 is a photomicrograph of the eye of FIG. 1 after surgery.

With reference to FIG. 2, as soon as posterior hyaloid separation occurs, some of the agent suspended in the midvitreous cavity settles on the dependent retinal surface, confirming creation of the posterior vitreous detachment. The tip of the vitrectomy port is just above the triamcinolone granules. Upon completion of the vitrectomy procedure (removal of the vitreous and the posterior hyaloid), most of the vitreous is removed in the back of the eye, leaving some vitreous remaining in the front of the eye (in the vitreous "skirt"). If the agent is a corticosteroid, any agent remaining in the anterior vitreous provides a therapeutic benefit in the post-operative period by keeping the eye "quiet" i.e., preventing an inflammatory process. Additionally, since the dose initially injected is below the toxic dose, the dose remaining is substantially less than the toxic dose (one to three tenths of the toxic dose) and thus there is no associated toxicity.

Figure 3:
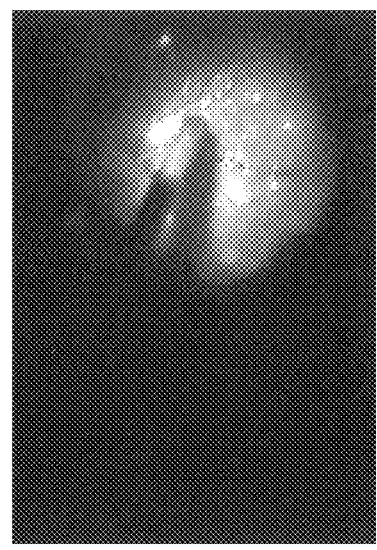
FIG. 3 is a photomicrograph of the eye of FIG. 2 showing agent removal.

With reference to FIG. 3, the remaining agent is easily removed from the retinal surface by gentle aspiration, for example, by suction from the vitrector port or extrusion cannula. The vitreous that has been removed is replaced by other fluid such as air or other gas, or silicone oil.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A surgical method to alleviate a structural disorder of an eye caused by the vitreous comprising
    injecting a composition consisting essentially of a corticosteroid as a vitreous delineating agent into the eye in an amount effective to render the vitreous visible for surgical correction, and
    surgically correcting the disorder by removing the vitreous wherein said corticosteroid is selected from the group consisting of dexamethasone, triamcinolone, hydrocortisone, cortisol, cortisone, corticosterone, 11-desoxycorticosterone, 11-desoxycortisol, aldosterone, prednisolone, 6α-methylprednisolone, paramethasone, betamethasone, fludrocortisone, tetrahydrocortisol, prednisone, methylprednisolone, salts and derivatives thereof, and combinations thereof.

2. The method of claim 1 wherein said agent is selected from the group consisting of a therapeutic agent, an inert agent, and combinations thereof.

3. The method of claim 1 wherein said agent is formulated as a vesicle selected from the group consisting of a liposome and a microsphere.

4. The method of claim 1 wherein said agent has a formulation selected from the group consisting of a solution, an emulsion, and a suspension.

5. The method of claim 2 wherein said therapeutic agent is selected from the group consisting of an anti-infective agent, an immunosuppressant agent, an antiproliferative agent, an anti-angiogenesis agent, and combinations thereof.

6. A surgical method to alleviate a structural disorder of an eye caused by the vitreous comprising
    injecting a composition consisting essentially of a corticosteroid formulation as a vitreous delineating agent into the eye in an effective amount to render the vitreous visible for surgical correction, and
    surgically correcting the disorder by removing the vitreous wherein said corticosteroid is selected from the group consisting of dexamethasone, triamcinolone, corticosterone, 11-desoxycorticosterone, 11-desoxycortisol, aldosterone, 6α-methylprednisolone, betamethasone, fludrocortisone, tetrahydrocortisol, prednisone, methylprednisolone, prednisolone, salts and derivatives thereof, and combinations thereof.

7. The method of claim 6 wherein the corticosteroid is incorporated in a vesicle selected from the group consisting of a microsphere and a liposome.

8. A composition for visualizing the vitreous in a mammalian eye during surgery consisting essentially of an injectable formulation of a corticosteroid as a vitreous delineating agent in an effective amount that associates with vitreous fibers in the eye to render the vitreous visible to a surgeon wherein said corticosteroid is selected from the group consisting of dexamethasone, triamcinolone, hydrocortisone, cortisol, cortisone, corticosterone, 11-desoxycorticosterone, 11-desoxycortisol, aldosterone, prednisolone, 6α-methylprednisolone, paramethasone, betamethasone, fludrocortisone, tetrahydrocortisol, prednisone, methylprednisolone, salts and derivatives thereof, and combinations thereof.

9. The composition of claim 8 wherein said formulation is translucent.

10. The composition of claim 8 wherein said formulation is opaque.

11. The composition of claim 8 wherein said formulation is semi-opaque.

12. The composition of claim 8 wherein said agent is a vesicle selected from the group consisting of a liposome and a microsphere.

13. The composition of claim 12 further comprising a therapeutic agent.

14. The composition of claim 8 injected during a vitrectomy.

15. The method of claim 1 wherein said corticosteroid is triamcinolone acetonide.

* * * * *